United States Patent
Leppard et al.

[11] Patent Number: 5,942,290
[45] Date of Patent: Aug. 24, 1999

[54] MOLECULAR COMPLEX COMPOUNDS OF ACYLPHOSPHINE OXIDE AND α-HYDROXY KETONES AS PHOTOINITIATORS

[75] Inventors: David George Leppard, Marly; Thomas Lloyd James, Frenkendorf, both of Switzerland; Nils Höck, Müllheim-Zunzingen; Manfred Köhler, Freiburg, both of Germany; Ronald Salathé, Magden, Switzerland

[73] Assignee: Ciba Specialty Chemicals Corporation, Tarrytown, N.Y.

[21] Appl. No.: 08/915,776

[22] Filed: Aug. 21, 1997

[30] Foreign Application Priority Data

Aug. 28, 1996 [CH] Switzerland ............ 2115/96

[51] Int. Cl.⁶ ............ C08K 3/20; C08L 67/06; C08F 2/50; C07F 9/53
[52] U.S. Cl. ............ 427/510; 427/519; 522/38; 522/42; 522/64; 522/75; 522/81; 522/107; 522/179; 522/181; 522/182; 560/254; 560/255; 560/53; 568/14; 568/15; 568/335; 568/336
[58] Field of Search ............ 522/64, 18, 38, 522/42, 107, 181, 182, 179, 81; 568/14, 15, 335, 336, 329; 560/254, 255, 53; 427/510, 519

[56] References Cited

U.S. PATENT DOCUMENTS

| | | | |
|---|---|---|---|
| 4,298,738 | 11/1981 | Lechtken et al. | 546/22 |
| 4,308,400 | 12/1981 | Felder et al. | 568/336 |
| 4,347,111 | 8/1982 | Gehlhaus et al. | 204/159.16 |
| 4,672,079 | 6/1987 | Li Bassi et al. | 522/35 |
| 4,710,523 | 12/1987 | Lechtken et al. | 522/14 |
| 4,792,632 | 12/1988 | Ellrich et al. | 568/15 |
| 5,218,009 | 6/1993 | Rutsch et al. | 522/16 |
| 5,723,512 | 3/1998 | Leppard et al. | 522/55 |

FOREIGN PATENT DOCUMENTS

| | | |
|---|---|---|
| 0003002 | 7/1979 | European Pat. Off. |
| 0007508 | 2/1980 | European Pat. Off. |
| 0057474 | 8/1982 | European Pat. Off. |
| 446175 | 9/1991 | European Pat. Off. |
| 0670323 | 9/1995 | European Pat. Off. |
| 19618720 | 11/1996 | Germany . |
| 2259704 | 3/1993 | United Kingdom . |
| 2292740 | 3/1996 | United Kingdom . |
| 2310855 | 9/1997 | United Kingdom . |
| 9607662 | 3/1996 | WIPO . |

OTHER PUBLICATIONS

Derwent Abstr. 95–110660/15 for JP 07033811.
Derwent Abstr. 94–363223/45 for JP 06286085.
Derwent Abstr. 91–126891 for JP 03160013.
Derwent Abst. 91–269010/37 of EP 446,175.
Derwent Abstract 68540 E/33 for EP 057474.
Derwent Abstr. 97–044005/05 for DE 19618720.

*Primary Examiner*—Susan W. Berman
*Attorney, Agent, or Firm*—David R. Crichton; Luther A. R. Hall

[57] ABSTRACT

Molecular complex compounds comprising a mono-, bis- or trisacylphosphine oxide compound with an α-hydroxy ketone compound are suitable as photoinitiators for the photopolymerization of free-radically polymerizable compounds.

17 Claims, No Drawings

MOLECULAR COMPLEX COMPOUNDS OF ACYLPHOSPHINE OXIDE AND α-HYDROXY KETONES AS PHOTOINITIATORS

The invention relates to molecular complex compounds comprising mono- and bisacylphosphine oxides with α-hydroxy ketones and to the use of these molecular complex compounds as photoinitiators.

Acylphosphine oxides have been described in the literature as photoinitiators. For example, EP-A 7 508 reveals the preparation and use of some monoacylphosphine oxides. Further monoacylphosphine oxides, and bisacylphosphine oxides, are known from U.S. Pat. No. 5,218,009. The preparation and use of bisacylphosphine oxide photoinitiators is disclosed, for example, in the U.S. Pat. Nos. 4,737,593 and 4,792,632 and in GB-A2259704. Trisacylphosphine oxide compounds are revealed, for example, in WO-A 96/7662. α-Hydroxy ketone compounds as photoinitiators are cited, for example, in the U.S. Pat. Nos. 4,347,111 and 4,672,079 and in EP-A 3002. The use of photoinitiator mixtures comprising acylphosphine oxides and α-hydroxy ketones is described, for example, in GB-A 2 259 704 or GB-A 2 292 740.

There is a need for readily obtainable, reactive and storage-stable photoinitiator compounds which can be incorporated readily into formulations that are to be polymerized.

It has now been found that molecular complex compounds comprising various photoinitiator compounds possess these properties.

The invention therefore provides molecular complex compounds comprising a mono-, bis- or trisacylphosphine oxide compound with an α-hydroxy ketone compound.

The molecular complex compounds can be prepared, for example, by generally known methods of growing crystals, for example from solution or melt methods. Such crystallization methods are known to the skilled worker and are also described in textbooks of chemistry, for example in Ullmann's Encyclopedia of Industrial Chemistry, Vol. A 8,127–131, Verlag Chemie, Weinheim-New York (1987) or Kirk-Othmer, Encyclopedia of Chemical Technology, Vol.7, 672–81, Verlag John Wiley & Sons, New York (1979).

In the case of the solution process, the molecular complex compound can be prepared, for example, by dissolving the two components (i.e. the acylphosphine oxide compound and the α-hydroxy ketone compound), with or without heating, in appropriate solvents or solvent mixtures and precipitating the molecular complex compounds which form, either by adding a solvent in which the resulting complex compound is of lower solubility or by cooling the solution very slowly.

It is judicious, for example, to cool a solution of the components which has been saturated at a relatively high temperature, in a vessel subject to uniform thermal conditioning, very slowly to a lower temperature. In this case the nucleation of the crystals can be initiated by rubbing on the wall of the vessel, for example.

It is also possible, for example, to remove continuously the solvent from a saturated solution of the components, for example by evaporation, in which case the formation of the molecular complex crystal begins.

The temperatures used in preparing the saturated solutions are dependent on the solvent or solvent mixture employed and range, for example, from room temperature to 150° C., in particular 50–100° C.

In preparing the molecular complex compounds the two components are preferably employed in a molar ratio of 1:1. However, it is also possible to employ the components in other molar ratios, for example from 5:1 to 1:5. In this case it is then possible, for example, for the mixture formed to comprise molecular complex compound and the component added in excess.

The choice of solvent in preparing the molecular complex compounds is guided by the particular melting point of the components. In the present case, particularly suitable solvents for the different photoinitiator compounds are aliphatic hydrocarbons, such as hexane, pentane, heptane, octane and isomer mixtures of these solvents. Also possible, however, is the use of aromatic hydrocarbons, for example xylene or toluene, etc.

It is advantageous to use polar additives, for example in amounts of 1–30%, for example 1–20%, especially 1–5%. Examples of such additives are ethyl acetate, methyl ethyl ketone, acetone, methyl isobutyl ketone and alcohols.

Also conceivable is the use of other polar solvents, for example linear and cyclic ethers, such as diethyl ether, tetrahydrofuran or dioxane.

It is also possible, for example, to use polar solvents, such as methyl ethyl ketone, and to precipitate the resulting complex compounds with water. These solvents can be employed in pure form or else may include water, for example as azeotrope. In other words, recycled solvents produced in the course of workup in an azeotropic mixture with water are also suitable.

Examples of other suitable solvents are boiling-limit petroleum spirits with an aromatics content of about 3–10%. These solvents can be admixed, for example, with the polar solvents described above. Other examples of suitable solvent mixtures are mixtures of isooctane and ethyl acetate, but also those which include water, as already mentioned above, for example methyl ethyl ketone and water.

The resultant molecular complex crystals are separated from the solution judiciously by means of customary separation measures, for example filtration. If the solvents used are high-boiling solvents, then in the course of filtration the precipitated molecular complex compounds are washed with a low-boiling solvent, for example hexane, in order to make it possible to dry the crystals. The crystals are judiciously dried at slightly elevated temperature and with application of a vacuum, in particular at 40–50° C. and about 50 mbar. It may also be judicious to wash the crystals in order to remove impurities. This is done, for example, using a solvent in which the crystals are of very low solubility and which is miscible with the mother liquor.

It is also possible, for example, to prepare the complex compound by adding the second component directly in the course of the preparation of one component, prior to its isolation and thus while it is still in solution, and to precipitate the complex compound by adding an appropriate solvent. In the preparation of the acylphosphine oxide compound, for example, the compound can be transferred after the oxidation step into an appropriate solvent, the α-hydroxy ketone compound added, and the molecular complex compound precipitated.

It is also possible, for example, to obtain the novel molecular complex compounds by melting the acylphosphine oxide compounds and α-hydroxy ketone compounds and then slowly cooling the melt. In this case it is possible, for example, first to prepare the mixture of the two components and then to melt the mixture, although each component can also be melted individually and the compounds mixed in the melted state. The temperatures are dependent on the melting points of the respective components and are, for example, from about 100° C. to 200° C. In some cases it is judicious to seed the melt with crystals of the molecular complex compounds obtained from the solvent method. Such seeding is carried out, for example, after the melt has been cooled to room temperature or else at the melting point of the molecular complex compound.

Melt methods of this kind for producing crystals are known to the skilled worker and are described, for example, in Ullmann's Encyclopedia of Industrial Chemistry, Vol. A 8, 121–127, Verlag Chemie, Weinheim-New York (1987).

When cooling the melt, especially when cooling the melt rapidly, amorphous modifications of the novel molecular complex compounds, for example, can also be obtained. For the preparation of certain molecular complex compounds the rapid cooling may prove to be in-judicious, since with some compounds the formation of the complex is slow. In the case of rapid cooling, moreover, there is a greater probability of mixtures forming between the complex compound and one of its components.

It is also conceivable, for example, that polymorphous crystal forms of the molecular complex compounds are formed, or, for example, crystals of molecular complex compounds which contain "guest molecules", for example solvent, depending on the crystallization method. However, these mixtures are also suitable as initiators for photopolymerization.

The molecular complexes are in general associated by way of hydrogen bonds between the H atoms of the OH group of the hydroxy ketone and the oxygen atom which is attached to the P atom in the phosphine oxide compound.

Preference is given to molecular complex compounds in which the mono-, bis- or trisacylphosphine oxide compound is a compound of the formula I

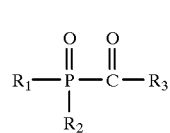

(I)

$R_1$ and $R_2$ independently of one another are $C_1$–$C_{18}$alkyl, $C_2$–$C_8$alkyl interrupted by one or more O atoms, phenyl-substituted $C_1$–$C_4$alkyl, $C_2$–$C_{18}$alkenyl, phenyl which is unsubstituted or is substituted from one to five times by halogen, hydroxyl, $C_1$–$C_8$alkyl and/or $C_1$–$C_8$alkoxy, naphthyl which is unsubstituted or substituted from one to five times by halogen, hydroxyl, $C_1$–$C_8$alkyl and/or $C_1$–$C_8$alkoxy, biphenyl which is unsubstituted or substituted from one to five times by halogen, hydroxyl, $C_1$–$C_8$alkyl and/or $C_1$–$C_8$alkoxy, or are $C_3$–$C_{12}$cycloalkyl, an O-, S- or N-containing 5- or 6-membered heterocyclic ring or a group $COR_3$; or $R_1$ is — $OR_4$ or a group

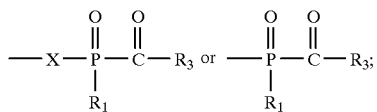

or $R_1$ and $R_2$ together are $C_4$–$C_8$alkylene and, with the P atom to which they are attached, form a ring structure;

$R_3$ is $C_1$–$C_{18}$alkyl, $C_3$–$C_{12}$cycloalkyl, $C_2$–$C_{18}$alkenyl, phenyl, naphthyl or biphenyl each of which is unsubstituted or substituted from one to four times by $C_1$–$C_8$alkyl, $C_1$–$C_8$alkoxy, $C_1$–$C_8$alkylthio and/or halogen, or is an O—, S— or N-containing 5- or 6-membered heterocyclic ring or a group

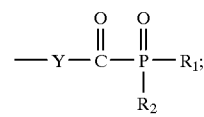

$R_4$ is $C_1$–$C_8$alkyl, phenyl, naphthyl or phenyl-$C_1$–$C_8$alkyl;

Y is phenylene, $C_1$–$C_{12}$alkylene, cyclopentylene or cyclohexylene;

X is $C_1$–$C_{18}$alkylene, $C_2$–$C_{18}$alkylene which is interrupted one or more times by —O—, —S—, —NR$_5$—,

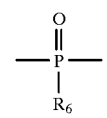

or —SO$_2$—, or is $C_1$–$C_6$alkylene which is substituted by Cl, F, $C_1$–$C_4$alkoxy, $COOR_7$, phenyl, phenyl-$C_1$–$C_4$alkyl, naphthyl-$C_1$–$C_4$alkyl, $C_1$–$C_4$alkylphenyl, $C_1$–$C_4$alkylnaphthyl, phenyl-$C_1$–$C_4$alkoxy, naphthyl-$C_1$–$C_4$alkoxy, $C_1$–$C_4$alkoxy-$C_1$–$C_4$alkoxy and/or CN, or X is $C_1$–$C_8$alkylene which is substituted by one or two radicals of the formula A

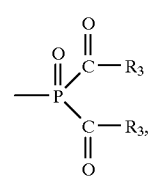

(A)

X is a group of the formula $A_1$–$A_9$

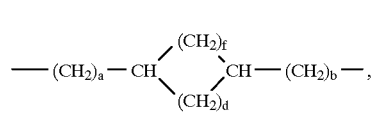

(A$_1$)

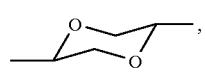

(A$_2$)

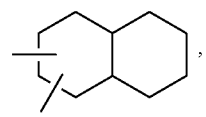

(A$_3$)

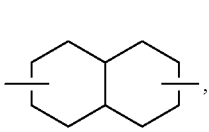

(A$_4$)

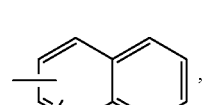

(A$_5$)

-continued

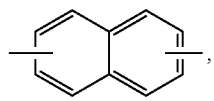
(A₆)

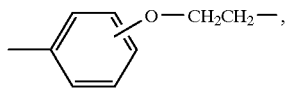
(A₇)

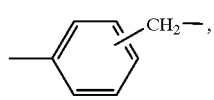
(A₈)

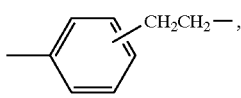
(A₉)

a and b independently of one another are 0 or 1 and the sum of d and f is a number from 3 to 8, neither d nor f being 0, or X is a group —CH₂—CH=CH—CH₂— or —CH₂—C≡C—CH₂—, or is phenylene which is unsubstituted or substituted from one to three times by Cl, F, C₁–C₄alkyl and/or C₁–C₄alkoxy, or is xylylene,

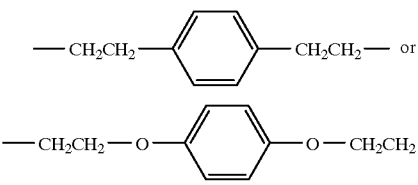

or
X is a group of the formula A₁₀–A₁₃

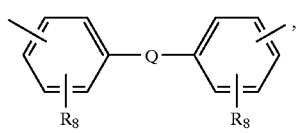
(A₁₀)

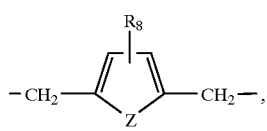
(A₁₁)

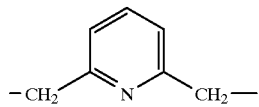
(A₁₂)

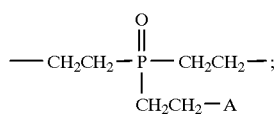
(A₁₃)

Q is a single bond, CR₉R₁₀, —O—, —S—, —NR₅—, —SO2—, —(CH₂)$_p$— or —CH=CH—;

p is a number from 2–12;
Z is O or S;
R₅ is hydrogen, C₁–C₁₂alkyl or phenyl;
R₆ is C₁–C₄alkyl or phenyl;
R₇ is C₁–C₁₂alkyl, C₂–C₁₈alkyl interrupted one or more times by —O—, or is benzyl, phenyl, cyclopentyl or cyclohexyl;
R₈ is hydrogen, C₁–C₄alkyl, C₁–C₄alkoxy or halogen;
R₉ is hydrogen or C₁–C₄alkyl; and
R₁₀ is hydrogen, methyl or ethyl.

C₁–C₁₈alkyl can be linear or branched and is, for example, methyl, ethyl, propyl, isopropyl, butyl, isobutyl, sec.-butyl, tert.-butyl, pentyl, isopentyl, hexyl, heptyl, octyl, nonyl, decyl, dodecyl or octadecyl. Preference is given to C₁–C₁₂, for example C₁–C₈ or C₁–C₆, especially C₁–C₄alkyl.

C₁–C₁₂, C₁–C₈ and C₁–C₄alkyl can have the same meanings as indicated above up to the corresponding number of C atoms.

C₂–C₁₈alkyl interrupted by one or more O atoms is interrupted, for example, from 1 to 5 times, for example 1 to 3 times or once or twice by —O—. This results as in structural units such as, for example, —O(CH₂)₂OH, —O(CH₂)₂OCH₃, —O(CH₂CH₂O)₂CH₂CH₃, —CH₂—O—CH₃, —CH₂CH₂O—CH₂CH₃, —[CH₂CH₂O]$_y$—CH₃, where y=1 to 5, —(CH₂CH₂O)₅CH₂CH₃, —CH₂—CH(CH₃)—O—CH₂—CH₂CH₃ or —CH₂—CH(CH₃)—O—CH₂—CH₃.

Phenyl-substituted C₁–C₄alkyl is, for example, benzyl, 2-phenylethyl, 3-phenylpropyl, α-methylbenzyl or α,α-dimethylbenzyl, especially benzyl.

Phenyl-C₁–C₈alkyl is, for example, benzyl, phenylethyl, α-methylbenzyl, phenylpentyl, phenylhexyl, phenyloctyl or α,α-dimethylbenzyl, especially benzyl.

Phenyl-C₁–C₄alkyl has the definitions given above up to the appropriate number of C atoms. Preference is given to phenyl-C₁–C₄alkyl, especially phenyl-C₁–C₂alkyl.

C₂–C₁₈alkenyl can be linear or branched and there can be more than one unsaturated bond in the molecule. Examples are vinyl, allyl, methylvinyl, butenyl, butadienyl, pentenyl, hexenyl, heptenyl, octenyl, nonenyl, decenyl, dodecenyl or octadecenyl.

C₁–C₈alkoxy can be linear or branched and is, for example, methoxy, ethoxy, propoxy, isopropoxy, butoxy, isobutoxy, sec.-butoxy, tert.-butoxy, pentoxy, isopentoxy, hexyloxy, heptyloxy or octyloxy. Preference is given, for example, to C₁–C₆ or, in particular, C₁–C₄alkoxy. C₁–C₆alkoxy and C₁–C₄alkoxy can have the same definitions as indicated above up to the appropriate number of C atoms.

C₁–C₄alkoxy-C₁–C₄alkoxy is, for example, methoxyethoxy, methoxypropoxy, methoxybutoxy, ethoxymethoxy, ethoxyethoxy, ethoxypropoxy, ethoxybutoxy, propoxymethoxy, propoxyethoxy, propoxypropoxy, propoxybutoxy, butoxymethoxy, butoxyethoxy, butoxypropoxy or butoxybutoxy, especially methoxyethoxy and ethoxyethoxy.

C₁–C₈alkylthio can be linear or branched and is, for example, methylthio, ethylthio, propylthio, isopropylthio, butylthio, tert-butylthio, hexylthio or octylthio, especially methylthio.

Halogen is, for example, chlorine, bromine and iodine, especially chlorine.

Substituted phenyl is substituted from one to five times, for example once, twice or three times, especially once or twice, on the phenyl ring. Substitution takes place, for example, in positions 2, 3, 4, 5, 2,4, 2,5, 2,6, 3,4, 3,5, 2,4,6 or 3,4,5 of the phenyl ring. C₁–C₈alkyl, C₁–C₄alkyl-, $C_1$–$C_8$alkoxy, $C_1$–$C_8$alkylthio and $C_1$–$C_4$alkoxy substitutents can have the definitions indicated above. Examples of substituted phenyl are tolyl, xylyl, 4-methoxyphenyl, 2,4- and 2,5-dimethoxyphenyl, ethylphenyl and 4-alkoxy-2-methylphenyl.

Examples of $C_3$–$C_{12}$cycloalkyl are cyclopentyl, cyclohexyl, cycloheptyl, cyclooctyl, cyclononyl, cyclodecyl or cyclododecyl, preferably cyclopentyl and cyclohexyl.

$R_1$ and $R_2$ as an O—, S—or N-containing 5- or 6-membered heterocyclic ring are, for example, furyl, thienyl, pyrrolyl, oxinyl, dioxinyl or pyridyl.

If $R_1$ and $R_2$ together are $C_4$–$C_8$alkylene and, with the P atom to which they are attached, form a ring structure then this structure can include not just simple rings but also bridged rings, for example

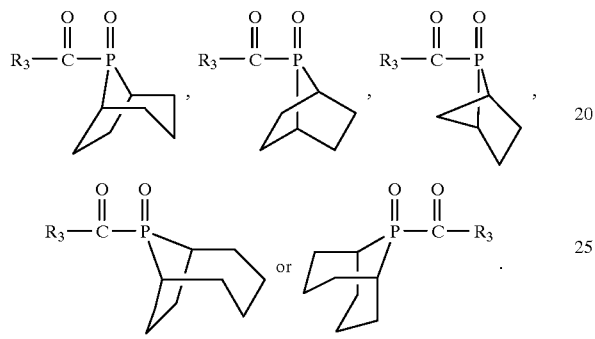

X as $C_1$–$C_{18}$alkylene is linear or branched alkylene, for example methylene, ethylene, propylene, isopropylene, n-butylene, sec-butylene, isobutylene, tert-butylene, pentylene, hexylene, heptylene, octylene, nonylene, decylene, dodecylene, tetradecylene, heptadecylene or octadecylene. In particular, X is $C_1$–$C_{12}$alkylene, for example ethylene, decylene,

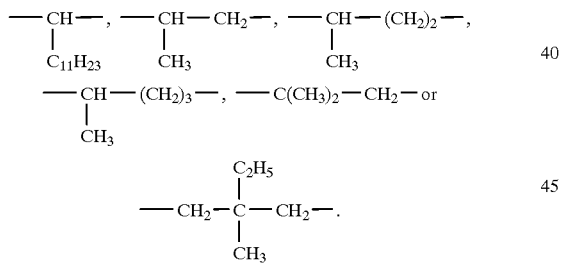

Interruption of X as $C_2$–$C_{18}$alkylene by —O—, —S—, —$NR_5$—, $$-\underset{\underset{R_6}{|}}{\overset{\overset{O}{\|}}{P}}-$$

or —$SO_2$— results, for example, in structural units such as —$CH_2$—O—$CH_2$—, —$CH_2CH_2$—O—$CH_2CH_2$—, —[$CH_2CH_2O$]$_y$—, where y=1–9, —($CH_2CH_2O$)$_7CH_2CH_2$—, —$CH_2$—CH($CH_3$)—O—$CH_2$—CH($CH_3$)—, —$CH_2$—S—$CH_2$—, —$CH_2CH_2$—S—$CH_2CH_2$—, —$CH_2CH_2CH_2$—S—$CH_2CH_2CH_2$—, —($CH_2$)$_3$—S—($CH_2$)$_3$—S—($CH_2$)$_3$—, —$CH_2$—($NR_5$)—$CH_2$—, —$CH_2CH_2$—($NR_5$)—$CH_2CH_2$—, —$CH_2$—(P(O)$R_6$)—$CH_2$—, —$CH_2CH_2$—(P(O)$R_6$)—$CH_2CH_2$—,

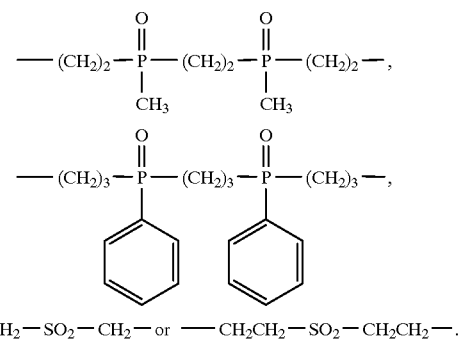

Examples of $C_1$–$C_8$alkylene which is substituted by one or two radicals of the formula A are

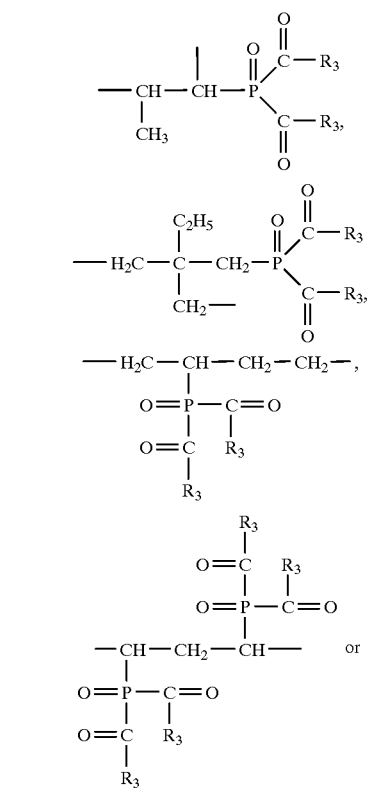

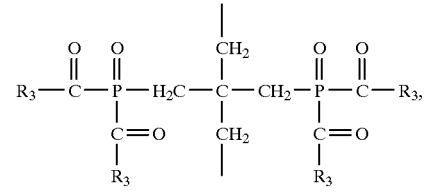

in which $R_3$ is as defined above.

Naphthyl-$C_1$–$C_4$alkyl is, for example, naphthylmethyl, naphthylethyl, naphthyl(1-methyl)eth-1-yl or naphthyl(1,1-dimethyl)eth-1-yl, especially naphthylmethyl.

$C_1$–$C_4$alkylphenyl is, for example, tolyl, xylyl, mesityl, ethylphenyl or diethylphenyl, preferably tolyl or mesityl.

$C_1$–$C_4$alkylnaphthyl is naphthyl substituted by methyl, ethyl and/or propyl or butyl.

Phenyl-$C_1$–$C_4$alkoxy is, for example, benzyloxy, phenylethyloxy, α-methylbenzyloxy or α,α-dimethylbenzyloxy, especially benzyloxy.

Naphthyl-$C_1$–$C_4$alkoxy is, for example, naphthylmethyloxy or naphthylethyloxy.

Examples of groups of the formula $A_1$ in which the sum of d and f is from 3 to 8 are:

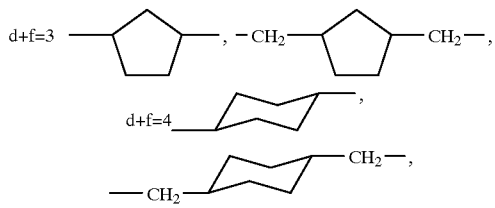

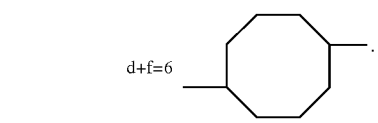

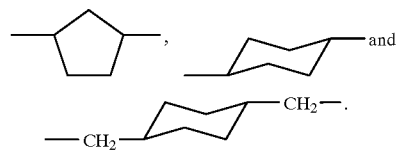

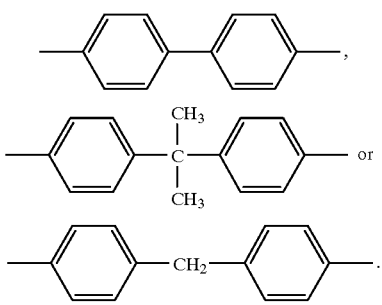

Preferred groups of the formula $A_{10}$ are

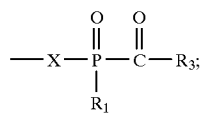

The preparation of acylphosphine oxide compounds of the formula I is known to the skilled worker and is described, for example, in EP-A 7 508, in U.S. Pat. Nos. 5,218,009, 4,737,593 and 4,792,632, in GB-A 2 259 704 and in WO-A 96/7662.

Preference is given to compounds of the formula I in which $R_1$ and $R_2$ independently of one another are $C_1$–$C_{12}$alkyl, benzyl, phenyl which is unsubstituted or substituted from one to four times by halogen, especially Cl, $C_1$–$C_8$alkyl and/or $C_1$–$C_8$alkoxy, or are cyclohexyl or $COR_3$, or $R_1$ is $OR_4$ or

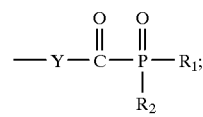

$R_3$ is phenyl which is unsubstituted or substituted from one to four times by $C_1$–$C_8$alkyl, especially $C_1$–$C_4$alkyl, $C_1$–$C_8$alkoxy, $C_1$–$C_8$alkylthio, especially $C_1$–$C_4$alkylthio, and/or halogen, especially chlorine, or is a group

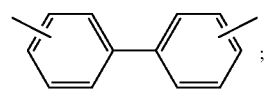

$R_4$ is $C_1$–$C_8$alkyl, especially $C_1$–$C_4$alkyl, phenyl or benzyl;

X is $C_1$–$C_{18}$alkylene, especially $C_6$–$C_{10}$alkylene, or a group

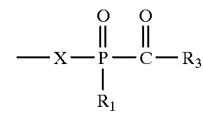

and Y is phenylene, $C_2$–$C_{12}$alkylene or cyclohexylene.

Other compounds of the formula I that are of interest are those in which $R_1$ and $R_2$ independently of one another are $C_1$–$C_8$alkyl, phenyl which is unsubstituted or substituted from one to four times by $C_1$–$C_4$alkyl and/or $C_1$–$C_8$alkoxy, or are cyclohexyl or a group $COR_3$, or $R_1$ is a group

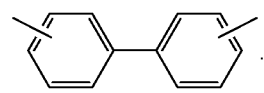

or —$OR_4$; $R_3$ is phenyl which is unsubstituted or substituted from one to four times by methyl and/or methoxy; $R_4$ is methyl, ethyl or phenyl; and X is $C_6$–$C_{10}$alkylene or

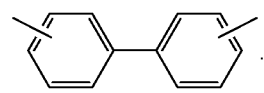

Notable compounds of the formula I are those in which $R_1$ is $COR_3$, $R_2$ is $C_1$–$C_{18}$alkyl and $R_3$ is phenyl which is substituted two or three times by $C_1$–$C_4$alkyl or $C_1$–$C_4$alkoxy.

Also of particular interest are those compounds of the formula I in which $R_1$ is $COR_3$, $R_2$ is phenyl which is unsubstituted or substituted by $C_1$–$C_4$alkyl and/or $C_1$–$C_4$alkoxy and $R_3$ is phenyl which is substituted two or three times by $C_1$–$C_4$alkyl or $C_1$–$C_4$alkoxy.

Compounds of the formula I are of particular interest when the substitution of $R_3$ as phenyl is in positions 2,6 or 2,4,6.

Examples of compounds of the formula I which are suitable for preparing the molecular complex compounds are bis(2,6-dimethoxybenzoyl)phenylphosphine oxide,
bis(2,6-dimethoxybenzoyl)(2,4,4-trimethylpentyl) phosphine oxide,
bis(2,6-dimethoxybenzoyl)-n-butylphosphine oxide,
bis(2,6-dimethoxybenzoyl)-(2-methylprop-1-yl)phosphine oxide,
bis(2,6-dimethoxybenzoyl)-(1-methylprop-1-yl)phosphine oxide,
bis(2,6-dimethoxybenzoyl)-t-butylphosphine oxide,
bis(2,6-dimethoxybenzoyl)cyclohexylphosphine oxide,
bis(2,6-dimethoxybenzoyl)octylphosphine oxide,
bis(2-methoxybenzoyl)(2-methylprop-1-yl)phosphine oxide, bis(2-methoxybenzoyl)(1-methylprop-1-yl)phosphine oxide,
bis(2,6-diethoxybenzoyl)(2-methylprop-1-yl)phosphine oxide,
bis(2,6-diethoxybenzoyl)(1-methylprop-1-yl)phosphine oxide,
bis(2,6-dibutoxybenzoyl)(2-methylprop-1-yl)phosphine oxide,
bis(2,4-dimethoxybenzoyl)(2-methylprop-1-yl)phosphine oxide,
bis(2,4,6-trimethylbenzoyl)phenylphosphine oxide,
2,4,6-trimethylbenzoyidiphenylphosphine oxide,
bis(2,4,6-trimethylbenzoyl)(2,4-dipentoxyphenyl) phosphine oxide,
bis(2,6-dimethoxybenzoyl)benzylphosphine oxide,
bis(2,6-dimethoxybenzoyl)-2-phenylpropylphosphine oxide,
bis(2,6-dimethoxybenzoyl)-2-phenylethylphosphine oxide,
bis(2,6-dimethoxybenzoyl)benzylphosphine oxide,
bis(2,6-dimethoxybenzoyl)-2-phenylpropylphosphine oxide,
bis(2,6-dimethoxybenzoyl)-2-phenylethylphosphine oxide,
2,6-dimethoxybenzoylbenzylbutylphosphine oxide,
2,6-dimethoxybenzoylbenzyloctylphosphine oxide,
bis(2,4,6-trimethylbenzoyl)isobutylphosphine oxide and
2,6-dimethoxybenzoyl-2,4,6-trimethylbenzoyl-n-butylphosphine oxide.

The α-hydroxy ketone compounds are, in particular, compounds of the formula II

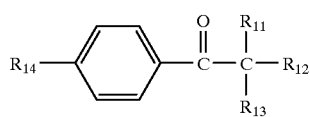

(II)

in which $R_{11}$ and $R_{12}$ independently of one another are hydrogen, $C_1$–$C_6$alkyl, phenyl, $C_1$–$C_6$alkoxy, $OSiR_{16}(R_{17})_2$ or —O(CH$_2$CH$_2$O)$_q$—$C_1$–$C_6$alkyl, or $R_{11}$ and $R_{12}$, together with the carbon atom to which they are attached, form a cyclohexyl ring;

q is a number from 1 to 20;

$R_{13}$ is OH, $C_1$–$C_{16}$alkoxy or —O(CH$_2$CH$_2$O)$_q$—$C_1$–$C_6$alkyl;

$R_{14}$ is hydrogen, $C_1$–$C_{18}$alkyl, $C_1$–$C_{18}$alkoxy, —OCH$_2$CH$_2$—OR$_{15}$, a group CH$_2$=C(CH$_3$)— or

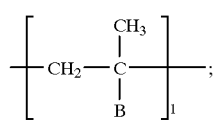

l is a number from 2 to 10;

B is the radical

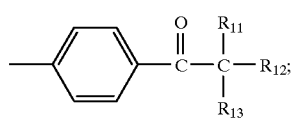

$R_{15}$ is hydrogen,

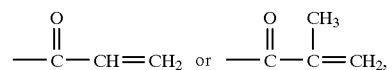

and $R_{16}$ and $R_{17}$ independently of one another are $C_1$–$C_8$alkyl or phenyl.

Examples of $C_1$–$C_{18}$alkyl, $C_1$–$C_6$alkyl, $C_1$–$C_4$alkyl, $C_1$–$C_{18}$alkoxy and $C_1$–$C_6$alkoxy have been indicated above.

The preparation of the α-hydroxy ketone compounds of the formula II is familiar to the skilled worker and is described, for example, in the U.S. Pat. Nos. 4,347,111 and 4,672,079 and in EP-A 3002.

Compounds of the formula II that are of interest are those in which $R_{11}$ and $R_{12}$ independently of one another are hydrogen, $C_1$–$C_6$alkyl or phenyl or $R_{11}$ and $R_{12}$, together with the carbon atom to which they are attached, form a cyclohexyl ring; $R_{13}$ is OH; and $R_{14}$ is hydrogen, $C_1$–$C_{12}$alkyl, $C_1$–$C_{12}$alkoxy, especially $C_1$–$C_4$alkoxy, —OCH$_2$CH$_2$OR$_{15}$, a group

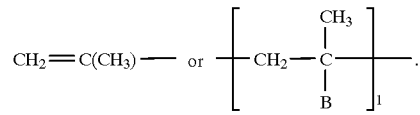

Preference is given to the compounds of the formula II in which $R_{11}$ and $R_{12}$ independently of one another are methyl or ethyl or $R_{11}$ and $R_{12}$, together with the carbon atom to which they are attached, form a cyclohexyl ring; $R_{13}$ is hydrogen and $R_{14}$ is hydrogen, $C_1$–$C_4$alkyl, $C_1$–$C_4$alkoxy or —OCH$_2$CH$_2$OH.

Examples of compounds of the formula II which are suitable for preparing the molecular complex compounds are α-hydroxycyclohexyl phenyl ketone,
2-hydroxy-2-methyl-1-phenylpropanone,
2-hydroxy-2-methyl-1-(4-isopropylphenyl)propanone,
2-hydroxy-2-methyl-1-(4-dodecylphenyl)propanone and
2-hydroxy-2-methyl-1-[(2-hydroxyethoxy)phenyl] propanone.

Preferred molecular complex compounds are those comprising a mono- or bisacylphosphine oxide compound of the formula I

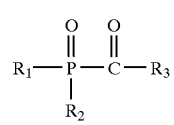

(I)

in which $R_1$ and $R_2$ independently of one another are $C_1$–$C_{12}$alkyl, phenyl which is unsubstituted or substituted once or twice by $C_1$–$C_8$alkyl and/or $C_1$–$C_8$alkoxy, or are COR$_3$; $R_3$ is a radical

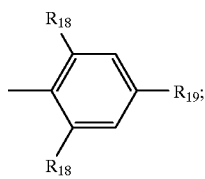

$R_{18}$ is $C_1$–$C_4$alkyl, especially methyl, or $C_1$–$C_4$alkoxy, especially methoxy; and $R_{19}$ is hydrogen or $C_1$–$C_4$alkyl, especially methyl;

and an α-hydroxy ketone compound of the formula II

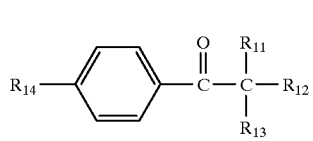

(II)

in which $R_{11}$ and $R_{12}$ independently of one another are $C_1$–$C_4$alkyl or $R_1$ and $R_2$, together with the carbon atom to which they are attached, form a cyclohexyl ring; and $R_{14}$ is hydrogen.

Preference is given, furthermore, to molecular complex compounds in which the acylphosphine oxide compound is bis(2,6-dimethoxybenzoyl)(2,4,4-trimethyl-pentyl)-phosphine oxide or 2,4,6-trimethylbenzoyldiphenylphosphine oxide and the α-hydroxy ketone compound is a compound of the formula II in which $R_{11}$ and $R_{12}$ are $C_1$–$C_4$alkyl or $R_{11}$ and $R_{12}$, together with the C atom to which they are attached, form a cyclohexyl ring, $R_{13}$ is OH and $R_{14}$ is hydrogen.

Also of interest are molecular complex compounds in which the acylphosphine oxide compound is bis(2,6-dimethoxybenzoyl)(2,4,4-trimethylpentyl)phosphine oxide, bis(2,4,6-trimethylbenzoyl)(2,4-dihexyloxyphenyl) phosphine oxide, bis(2,4,6-trimethylbenzoyl)(4-ethoxyphenyl)phosphine oxide or 2,4,6-trimethylbenzoyldiphenylphosphine oxide and the α-hydroxy ketone compound is α-hydroxycyclohexyl phenyl ketone or 2-hydroxy-2-methyl-1-phenylpropan-1-one.

Of particular interest are molecular complex compounds comprising bis(2,6-dimethoxybenzoyl)(2,4,4-trimethylpentyl) phosphine oxide and 2-hydroxy-2-methyl-1-phenylpropanone;

bis(2,6-dimethoxybenzoyl)(2,4,4-trimethylpentyl) phosphine oxide and α-hydroxycyclohexyl phenyl ketone;

bis(2,4,6-trimethylbenzoyl)phenylphosphine oxide and α-hydroxycyclohexyl phenyl ketone;

bis(2,4,6-trimethylbenzoyl)phenylphosphine oxide and 2-hydroxy-2-methyl-1-phenylpropanone;

2,4,6-trimethylbenzoyldiphenylphosphine oxide and α-hydroxycyclohexyl phenyl ketone;

2,4,6-trimethylbenzoyldiphenylphosphine oxide and 2-hydroxy-2-methyl-1-phenylpropanone;

bis(2,4,6-trimethylbenzoyl)(4-ethoxyphenyl)phosphine oxide and α-hydroxycyclohexyl phenyl ketone;

bis(2,4,6-trimethylbenzoyl)(2,4-dipentoxyphenyl) phosphine oxide and α-hydroxycyclohexyl phenyl ketone;

bis(2,4,6-trimethylbenzoyl)(2,4-dihexyloxyphenyl) phosphine oxide and α-hydroxy-cyclohexyl phenyl ketone;

bis(2,4,6-trimethylbenzoyl)(2,4-dipentoxyphenyl) phosphine oxide and 2-hydroxy-2-methyl-1-phenylpropanone;

bis(2,4,6-trimethylbenzoyl)(2-methylpropyl)phosphine oxide and α-hydroxycyclohexyl phenyl ketone;

bis(2,4,6-trimethylbenzoyl)(2-methylpropyl)phosphine oxide and 2-hydroxy-2-methyl-1-phenylpropanone;

bis(2,6-dimethoxybenzoyl)(2-methylpropyl)phosphine oxide and 2-hydroxy-2-methyl-1-phenylpropanone and bis(2,6-dimethoxybenzoyl)(2-methylpropyl)phosphine oxide and α-hydroxycyclohexyl phenyl ketone.

In accordance with the invention the molecular complex compounds can be used as photo-initiators for the photopolymerization of ethylenically unsaturated compounds or of mixtures which comprise such compounds.

This use may also be practised in combination with another photoinitiator and/or with other additives.

The invention therefore also provides photopolymerizable compositions comprising (a) at least one ethylenically unsaturated photopolymerizable compound, and (b) as photoinitiator, at least one molecular complex compound comprising a mono-, bis- or trisacylphosphine oxide compound with an α-hydroxy ketone compound, it being possible for the composition to comprise other photoinitiators and/or other additives in addition to component (b).

The unsaturated compounds may contain one or more olefinic double bonds. They may be of low molecular mass (monomeric) or of relatively high molecular mass (oligomeric). Examples of monomers containing a double bond are alkyl or hydroxyalkyl acrylates or methacrylates, for example methyl, ethyl, butyl, 2-ethylhexyl or 2-hydroxyethyl acrylate, isobornyl acrylate, or methyl or ethyl methacrylate. Silicone acrylates are also of interest. Further examples are acrylonitrile, acrylamide, methacrylamide, N-substituted (meth)acrylamides, vinyl esters such as vinyl acetate, vinyl ethers such as isobutyl vinyl ether, styrene, alkyl- and halostyrenes, N-vinylpyrrolidone, vinyl chloride or vinylidene chloride.

Examples of monomers containing two or more double bonds are the diacrylates of ethylene glycol, propylene glycol, neopentyl glycol, hexamethylene glycol and bisphenol A, 4,4'-bis-(2-acryloyloxyethoxy)diphenylpropane, trimethylolpropane triacrylate, pentaerythritol triacrylate or tetraacrylate, vinylacrylate, divinylbenzene, divinyl succinate, diallyl phthalate, triallyl phosphate, triallyl isocyanurate or tris(2-acryloylethyl) isocyanurate.

Examples of relatively high molecular mass (oligomeric) polyunsaturated compounds are acrylicized epoxy resins, and polyesters, polyurethanes and polyethers which are acrylicized or contain vinyl ether or epoxy groups. Further examples of unsaturated oligomers are unsaturated polyester resins which are mostly prepared from maleic acid, phthalic acid and one or more diols and have molecular weights of from about 500 to 3000. In addition it is also possible to employ vinyl ether monomers and vinyl ether oligomers, and also maleate-terminated oligomers having polyester, polyurethane, polyether, polyvinyl ether and epoxy main chains. Combinations of vinyl ether group-containing oligomers and polymers as are described in WO 90/01512 are of particular suitability. However, copolymers of vinyl ether and maleic acid-functionalized monomers are also appropriate. Such unsaturated oligomers can also be referred to as prepolymers.

Examples of particularly suitable compounds are esters of ethylenically unsaturated carboxylic acids and polyols or polyepoxides, and polymers containing ethylencially unsaturated groups in the chain or in side groups, for example unsaturated polyesters, polyamides and polyurethanes and copolymers thereof, polybutadiene and butadiene copolymers, polyisoprene and isoprene copolymers, polymers and copolymers containing (methy)acrylic groups in side chains, and also mixtures of one or more such polymers.

Examples of unsaturated carboxylic acids are acrylic, methacrylic, crotonic, itaconic and cinnamic acid and unsaturated fatty acids such as linolenic acid or oleic acid. Acrylic and methacrylic acid are preferred.

Suitable polyols are aromatic and, in particular, aliphatic and cycloaliphatic polyols. Examples of aromatic polyols are hydroquinone, 4,4'-dihydroxybiphenyl, 2,2-di(4-hydroxyphenyl)-propane, and also novolaks and resols. Examples of polyepoxides are those based on said polyols, especially aromatic polyols and epichlorohydrin. Other suitable polyols include polymers and copolymers which contain hydroxyl groups in the polymer chain or in side groups, for example polyvinyl alcohol and copolymers thereof or poly(hydroxyalkyl methacrylates) or copolymers thereof. Further suitable polyols are oligoesters containing hydroxyl end groups.

Examples of aliphatic and cycloaliphatic polyols are alkylenediols, preferably having 2 to 12 C atoms, such as ethylene glycol, 1,2- or 1,3-propanediol, 1,2-, 1,3- or 1,4-butanediol, pentanediol, hexanediol, octanediol, dodecanediol, diethylene glycol, triethylene glycol, polyethylene glycols having molecular weights from preferably 200 to 1500, 1,3-cyclopentanediol, 1,2-, 1,3- or 1,4-cyclohexanediol, 1,4-dihydroxymethylcyclohexane, glycerol, tris(β-hydroxyethyl)amine, trimethylolethane, trimethylolpropane, pentaerythritol, dipentaerythritol and sorbitol.

The polyols may be esterified in part or in whole with one or with different unsaturated carboxylic acids; in partial esters, the free hydroxyl groups can be modified, for example etherified or esterified with other carboxylic acids.

Examples of esters are:

Trimethylolpropane triacrylate, trimethylolethane triacrylate, trimethylolpropane trimethacrylate, trimethylolethane trimethacrylate, tetramethylene glycol dimethacrylate, triethylene glycol dimethacrylate, tetraethylene glycol diacrylate, pentaerythritol diacrylate, pentaerythritol triacrylate, pentaerythritol tetraacrylate, dipentaerythritol diacrylate, dipentaerythritol triacrylate, dipentaerythritol tetraacrylate, dipentaerythritol pentaacrylate, dipentaerythritol hexaacrylate, tripentaerythritol octaacrylate, pentaerythritol dimethacrylate, pentaerythritol trimethacrylate, dipentaerythritol dimethacrylate, dipentaerythritol tetramethacrylate, tripentaerythritol octamethacrylate, pentaerythritol diitaconate, dipentaerythritol trisitaconate, dipentaerythritol pentaitaconate, dipentaerythritol hexaitaconate, ethylene glycol diacrylate, 1,3-butanediol diacrylate, 1,3-butanediol dimethacrylate, 1,4-butanediol diitaconate, sorbitoltriacrylate, sorbitol tetraacrylate, pentaerythritol-modified triacrylate, sorbitol tetramethacrylate, sorbitol pentaacrylate, sorbitol hexaacrylate, oligoester acrylates and methacrylates, glycerol di- and triacrylate, 1,4-cyclohexane diacrylate, bisacrylates and bismethacrylates of polyethylene glycol having molecular weights from 200 to 1500, or mixtures thereof.

Further suitable components (a) are the amides of identical or different unsaturated carboxylic acids with aromatic, cycloaliphatic and aliphatic polyamines having preferably from 2 to 6, especially from 2 to 4 amino groups. Examples of such polyamines are ethylenediamine, 1,2- or 1,3-propylenediamine, 1,2-, 1,3- or 1,4-butylenediamine, 1,5-pentylenediamine, 1,6-hexylenediamine, octylenediamine, dodecylenediamine, 1,4-diaminocyclohexane, isophoronediamine, phenylenediamine, bisphenylenediamine, di-β-aminoethyl ether, diethylenetriamine, triethylenetetramine, di(β-aminoethoxy)- or di(β-aminopropoxy)ethane. Other suitable polyamines are polymers and copolymers with or without additional amino groups in the side chain, and oligoamides with amino end groups. Examples of unsaturated amides are: methylenebisacrylamide, 1,6-hexamethylenebisacrylamide, diethylenetriaminetrismethacrylamide, bis (methacrylamidopropoxy)ethane, β-methacrylamidoethyl methacrylate and N-[(β-hydroxyethoxy)ethyl]acrylamide.

Suitable unsaturated polyesters and polyamides are derived, for example, from maleic acid and diols or diamines. Some of the maleic acid may be replaced by other dicarboxylic acids. They can be employed together with ethylenically unsaturated comonomers, for example styrene. The polyesters and polyamides may also be derived from dicarboxylic acids and ethylenically unsaturated diols or diamines, in particular from relatively long-chain compounds containing, for example, 6 to 20 C atoms. Examples of polyurethanes are those built up from saturated or unsaturated diisocyanates and from unsaturated or saturated diols.

Polybutadiene and polyisoprene and copolymers thereof are known. Examples of suitable comonomers are olefins such as ethylene, propene, butene, hexene, (meth)acrylate, acrylonitrile, styrene and vinyl chloride. Polymers containing (meth)acrylate groups in the side chain are also known. These may be, for example, products of the reaction of novolak-based epoxy resins with (meth)acrylic acid, homopolymers or copolymers of vinyl alcohol or hydroxyalkyl derivatives thereof which have been esterified using (meth)acrylic acid, or homopolymers and copolymers of (meth)acrylates which have been esterified using hydroxyalkyl (meth)acrylates.

The photopolymerizable compounds may be employed alone or in any desired mixtures. Preference is given to mixtures of polyol (meth)acrylates.

It is also possible to add binders to the compositions according to the invention; this is particularly judicious if the photopolymerizable compounds are liquid or viscous substances. The quantity of binder may be, for example, 5–95% by weight, preferably 10–90% by weight and, in particular, 40–90% by weight, based on the overall solids content. The binder is chosen depending on the field of application and on the properties required therefor, such as the facility for development in aqueous and organic solvent systems, adhesion to substrates and sensitivity to oxygen.

Examples of suitable binders are polymers having a molecular weight of about 5000–2,000,000, preferably 10,000–1,000,000. Examples are homo- and copolymeric acrylates and methacrylates, for example copolymers of methyl methacrylate/ethyl acrylate/methacrylic acid, poly (alkyl methacrylates), poly(alkyl acrylates); cellulose esters and cellulose ethers, such as cellulose acetate, cellulose acetate butyrate, methylcellulose and ethylcellulose; polyvinylbutyral, polyvinylformal, cyclized rubber, polyethers, such as polyethylene oxide, polypropylene oxide and polytetrahydrofuran; polystyrene, polycarbonate, polyrurethane, chlorinated polyolefins, polyvinyl chloride, copolymers of vinyl chloride/vinylidene chloride, copolymers of vinylidene chloride with acrylonitrile, methyl methacrylate and vinyl acetate, polyvinyl acetate, copoly (ethylene/vinyl acetate), polymers such as polycaprolactam and poly(hexamethyleneadipamide), and polyesters such as poly(ethylene glycol terephthalate) and poly(hexamethylene glycol succinate).

The unsaturated compounds may also be used in mixtures with non-photopolymerizable film-forming components. These may be, for example, physically drying polymers or solutions thereof in organic solvents, for example nitrocellulose or cellulose acetobutyrate. However, these may also be chemically curable or heat-curable resins for example polyisocyanates, polyepoxides or melamine resins. The additional use of heat-curable resins is important for use in so-called hybrid systems, which are photopolymerized in a first step and crosslinked by thermal aftertreatment in a second step.

The photoinitiators according to the invention are also suitable as initiators for the curing of oxidatively drying systems, as are described, for example, in Lehrbuch der Lacke und Beschichtungen [Textbook of paints and coatings] Volume III, 296–328, Verlag W. A. Colomb in der Heenemann GmbH, Berlin-Oberschwandorf (1976).

The photopolymerizable mixtures may contain various additives in addition to the photoinitiator. Examples thereof are thermal inhibitors, which are intended to prevent premature polymerization, for example hydroquinone, hydroquinone derivatives, p-methoxyphenol, β-naphthol or sterically hindered phenols such as 2,6-di(tert-butyl)-p-cresol. The shelf life in the dark can be increased, for example, by using copper compounds such as copper naphthenate, copper stearate or copper octoate, phosphorus compounds, for example triphenylphosphine, tributylphosphine, triethyl phosphite, triphenyl phosphite or tribenzyl phosphite, quaternary ammonium compounds, for example tetramethylammonium chloride or trimethylbenzylammonium chloride, or hydroxylamine derivatives, for example N-diethylhydroxylamine. In order to exclude atmospheric oxygen during the polymerization, paraffin or similar wax-like substances can be added; these migrate to the surface on commencement of the polymerization because of their low solubility in the polymer, and form a transparent surface layer which prevents the ingress of air. Similarly, an oxygen-impermeable layer may be applied. Light stabilizers which can be added are UV absorbers, for example those of the hydroxyphenylbenzotriazole, hydroxyphenylbenzophenone, oxalamide or hydroxyphenyl-s-triazine type. These compounds can be employed individually or as mixtures with or without the use of sterically hindered amines (HALS).

Examples of such UV absorbers and light stabilizers are 1. 2-(2'-Hydroxyphenyl)benzotriazoles, for example 2-(2'-hydroxy-5'-methylphenyl)-benzotriazole, 2-(3',5'-di-tert-butyl-2'-hydroxyphenyl)benzotriazole, 2-(5'-tert-butyl-2'-hydroxyphenyl)benzotriazole, 2-(2'-hydroxy-5'-(1,1,3,3-tetramethylbutyl)phenyl)-benzotriazole, 2-(3',5'-di-tert-butyl-2'-hydroxyphenyl)-5-chlorobenzotriazole, 2-(3'-tert-butyl-2'-hydroxy-5'-methylphenyl)-5-chlorobenzotriazole, 2-(3'-sec-butyl-5'-tert-butyl-2'-hydroxyphenyl) benzotriazole, 2-(2'-hydroxy-4'-octoxyphenyl) benzotriazole, 2-(3',5'-di-tert-amyl-2'-hydroxyphenyl) benzotriazole, 2-(3',5'-bis(α,α-dimethylbenzyl)-2'-hydroxyphenyl)-benzotriazole, a mixture of 2-(3'-tert-butyl-2'-hydroxy-5'-(2-octyloxycarbonylethyl)phenyl)-5-chlorobenzotriazole, 2-(3'-tert-butyl-5'-[2-(2-ethylhexyloxy)carbonylethyl]-2'-hydroxyphenyl)-5-chlorobenzotriazole, 2-(3'-tert-butyl-2'-hydroxy-5'-(2-methoxycarbonylethyl)phenyl)-5-chlorobenzotriazole, 2-(3'-tert-butyl-2'-hydroxy-5'-(2-methoxycarbonylethyl) phenyl)-benzotriazole, 2-(3'-tert-butyl-2'-hydroxy-5'-(2-octyloxycarbonylethyl)phenyl)benzotriazole, 2-(3'-tert-butyl-5'-[2-(2-ethylhexyloxy)carbonylethyl]-2'-hydroxyphenyl)benzotriazole, 2-(3'-dodecyl-2'-hydroxy-5'-methylphenyl)benzotriazole, and 2-(3'-tert-butyl-2'-hydroxy-5'-(2-isooctyloxycarbonylethyl) phenylbenzotriazole, 2,2'-methylenebis[4-(1,1,3,3-tetramethylbutyl)-6-benzotriazol-2-ylphenol]; the transesterification product of 2-[3'-tert-butyl-5'-(2-methoxycarbonylethyl)-2'-hydroxyphenyl]benzotriazole with polyethylene glycol 300;

[R—$CH_2CH_2$—COO$(CH_2)_3$]$_2$ where R=3'-tert-butyl-4'-hydroxy-5'-2H-benzotriazol-2-ylphenyl.

2. 2-Hydroxybenzophenones, for example the 4-hydroxy, 4-methoxy, 4-octoxy, 4-decyloxy, 4-dodecyloxy, 4-benzyloxy, 4,2',4'-trihydroxy and 2'-hydroxy-4,4'-dimethoxy derivative.

3. Esters of substituted or unsubstituted benzoic acids, for example 4-tert-butyl-phenyl salicylate, phenyl salicylate, octylphenyl salicylate, dibenzoylresorcinol, bis(4-tert-butylbenzoyl)resorcinol, benzoylresorcinol, 2,4-di-tert-butylphenyl 3,5-di-tert-butyl-4-hydroxybenzoate, hexadecyl 3,5-di-tert-butyl-4-hydroxybenzoate, octadecyl 3,5-di-tert-butyl-4-hydroxybenzoate, 2-methyl-4,6-di-tert-butylphenyl 3,5-di-tert-butyl-4-hydroxybenzoate.

4. Acrylates, for example ethyl α-cyano-β,β-diphenylacrylate or isooctyl α-cyano-β,β-diphenylacrylate, methyl α-carbomethoxycinnamate, methyl α-cyano-β-methyl-p-methoxycinnamate or butyl α-cyano-β-methyl-p-methoxycinnamate, methyl α-carbomethoxy-p-methoxycinnamate and N-(β-carbomethoxy-β-cyanovinyl)-2-methylindoline.

5. Sterically hindered amines, for example bis(2,2,6,6-tetramethylpiperidyl) sebacate, bis(2,2,6,6-tetramethylpiperidyl) succinate, bis(1,2,2,6,6-pentamethylpiperidyl) sebacate, bis(1,2,2,6,6-pentamethylpiperidyl) n-butyl 3,5-di-tert-butyl-4-hydroxybenzylmalonate and succinic acid, the condensate of 1-hydroxyethyl-2,2,6,6-tetramethyl-4-hydroxypiperidine and succinic acid, the condensate of N,N'-bis(2,2,6,6-tetramethyl-4-piperidyl)hexamethylenediamine and 4-tertoctylamino-2,6-dichloro-1,3,5-s-triazine, tris(2,2,6,6-tetramethyl-4-piperidyl) nitrilotriacetate, tetrakis(2,2,6,6-tetramethyl-4-piperidyl) 1,2,3,4-butanetetraoate, 1,1'-(1,2-ethanediyl)bis-(3,3,5,5-tetramethylpiperazinone), 4-benzoyl-2,2,6,6-tetramethylpiperidine, 4-stearyloxy-2,2,6,6-tetramethylpiperidine, bis(1,2,2,6,6-pentamethylpiperidyl)-2-n-butyl-2-(2-hydroxy-3,5-di-tert-butylbenzyl) malonate, 3-n-octyl-7,7,9,9-tetramethyl-1,3,8-triazaspiro[4.5]decane-2,4-dione, bis(1-octyloxy-2,2,6,6-tetramethylpiperidyl) sebacate, bis(1-octyloxy-2,2,6,6-tetramethylpiperidyl) succinate, the condensate of N,N'-bis (2,2,6,6-tetramethyl-4-piperidyl)hexamethylenediamine and 4-morpholino-2,6-dichloro-1,3,5-triazine, the condensate of 2-chloro-4,6-di(4-n-butylamino-2,2,6,6-tetramethylpiperidyl)-1,3,5-triazine and 1,2-bis(3-aminopropylamino)ethane, the condensate of 2-chloro-4,6-di(4-n-butylamino-1,2,2,6,6-pentamethylpiperidyl)-1,3,5-triazine and 1,2-bis(3-aminopropylamino)ethane, 8-acetyl-3-dodecyl-7,7,9,9-tetramethyl-1,3,8-triazaspiro[4.5]decane-2,4-dione, 3-dodecyl-1-(2,2,6,6-tetramethyl-4-piperidyl) pyrrolidine-2,5-dione, 3-dodecyl-1-(1,2,2,6,6-pentamethyl-4-piperidyl)pyrrolidine-2,5-dione.

6. Oxalamides, for example 4,4'-dioctyloxyoxanilide, 2,2'-diethoxyoxanilide, 2,2'-dioctyloxy-5,5'-di-tert-butyloxanilide, 2,2'-didodecyloxy-5,5'-di-tert-butyloxanilide, 2-ethoxy-2'-ethyloxanilide, N,N'-bis(3-dimethylaminopropyl)oxalamide, 2-ethoxy-5-tert-butyl-2'-ethyloxanilide and its mixture with 2-ethoxy-2'-ethyl-5,4'- di-tert-butyloxanilide and mixtures of o- and p-methoxy and of o- and p-ethoxy-disubstituted oxanilides.

7. 2-(2-Hydroxyphenyl)-1.3.5-triazines, for example 2,4, 6-tris(2-hydroxy-4-octyloxyphenyl)-1,3,5-triazine, 2-(2-hydroxy-4-octyloxyphenyl)-4,6-bis(2,4-dimethylphenyl)-1, 3,5-triazine, 2-(2,4-dihydroxyphenyl)-4,6-bis(2,4-dimethylphenyl)-1,3,5-triazine, 2,4-bis(2-hydroxy-4-propyloxyphenyl)-6-(2,4-dimethylphenyl)-1,3,5-triazine, 2-(2-hydroxy-4-octyloxyphenyl)-4,6bis(4-methylphenyl)-1, 3,5-triazine, 2-(2-hydroxy-4-dodecyloxyphenyl)-4,6-bis(2, 4-dimethylphenyl)-1,3,5-triazine, 2-[2-hydroxy-4-(2-hydroxy-3-butyloxypropyloxy)phenyl]-4,6-bis(2,4-dimethylphenyl)-1,3,5-triazine, 2-[2-hydroxy-4-(2-hydroxy-3-octyloxypropyloxy)-phenyl]-4,6-bis(2,4-dimethylphenyl)-1,3,5-triazine and 2-[4-dodecyl/tridecyloxy(2-hydroxypropyl)oxy-2-hydroxyphenyl]-4,6-bis(2,4-dimethylphenyl)-1,3,5-triazine.

8. Phosphites and phosphonites, for example triphenyl phosphite, diphenyl alkyl phosphites, phenyl dialkyl phosphites, tris(nonylphenyl) phosphite, trilauryl phosphite, trioctadecyl phosphite, distearyl pentaerythritol diphosphite, tris(2,4-di-tert-butylphenyl) phosphite, diisodecyl pentaerythritol diphosphite, bis(2,4-di-tert-butylphenyl) pentaerythritol diphosphite, bis(2,6-di-tert-butyl-4-methylphenyl)pentaerythritol diphosphite, bisisodecyloxypentaerythritol diphosphite, bis(2,4-di-tert-butyl-6-methylphenyl)pentaerythritol diphosphite, bis(2,4, 6-tri-tert-butylphenyl)pentaerythritol diphosphite, tristearyl sorbitol triphosphite, tetrakis(2,4-di-tert-butylphenyl) 4,4'-biphenylene diphosphonite, 6-isooctyloxy-2,4,8,10-tetra-tert-butyl-12H-dibenzo[d,g]-1,3,2-dioxaphosphocin, 6-fluoro-2,4,8,10-tetra-tert-butyl-12-methyl-dibenzo[d,g]-1, 3,2-dioxaphosphocin, bis(2,4-di-tert-butyl-6-methylphenyl) methyl phosphite, bis(2,4-di-tert-butyl-6-methylphenyl) ethyl phosphite.

The invention therefore also provides a photopolymerizable composition comprising as photoinitiator at least one molecular complex compound comprising a mono-, bis- or tris-acylphosphine oxide compound with an α-hydroxy ketone compound, and also a UV absorber from the class of the hydroxyphenyl-s-triazines and/or hydroxyphenylbenzotriazoles and/or sterically hindered amines based on 2,2,6,6-tetramethylpiperidines.

To accelerate the photopolymerization it is possible to add amines, for example triethanolamine, N-methyldiethanolamine, ethyl p-dimethylaminobenzoate or Michler's ketone. The action of the amines can be intensified by the addition of aromatic ketones of the benzophenone type. Examples of amines which can be used as oxygen scavengers are substituted N,N-dialkylanilines as described in EP-A-339 841. Further accelerators, coinitiators and autoxidizers are thiols, thioethers, disulfides and phosphines as described, for example, in EP-A-438 123 and GB-A-2 180 358.

The photopolymerization can also be accelerated by the addition of photosensitizers which shift or broaden the spectral sensitivity. These are, in particular, aromatic carbonyl compounds such as benzophenone derivatives, thioxanthone derivatives, anthraquinone derivatives and 3-acylcoumarin derivatives and 3-(aroylmethylene) thiazolines, and also eosine, rhodamine and erythrosine dyes.

The curing process may be assisted, in particular, by compositions which are pigmented (for example with $TiO_2$), but also by the addition of a component which forms free radicals under thermal conditions, for example an azo compound such as 2,2'-azobis(4-methoxy-2,4-dimethylvaleronitrile), a triazine, diazo sulfide, pentazadiene or a peroxy compound such as a hydroperoxide or peroxycarbonate, for example t-butyl hydroperoxide, as described in EP-A 245 639, for example.

The compositions according to the invention may also contain a photoreducible dye, for example xanthene, benzoxanthene, benzothioxanthene, thiazine, pyronine, porphyrin or acridine dyes, and/or a trihalomethyl compound which can be cleaved by radiation. Similar compositions are described in, for example, EP-A-445 624.

Other conventional additives are—depending on the intended application—optical brighteners, fillers, pigments, dyes, wetting agents or levelling assistants. Thick and pigmented coatings can suitably be cured by the addition of glass microbeads or powdered glass fibres, as described in U.S. Pat. No. 5,013,768, for example.

The invention also relates to compositions comprising as component (a) at least one ethylenically unsaturated, photopolymerizable compound which is emulsified or dissolved in water.

Radiation-curable, aqueous prepolymer dispersions of this type are commercially available in many variations. This term is taken to mean a dispersion of water and at least one prepolymer dispersed therein. The concentration of the water in these systems is, for example, from 5 to 80% by weight, in particular from 30 to 60% by weight. The radiation-curable prepolymer or prepolymer mixture is present, for example, in concentrations of from 95 to 20% by weight, in particular from 70 to 40% by weight. The total of the percentages indicated for water and prepolymer in these compositions is in each case 100, to which are added the auxiliaries and additives in various amounts depending on the application.

The radiation-curable, water-dispersed, film-forming prepolymers, which are frequently also dissolved, are, for aqueous prepolymer dispersions, monofunctional or polyfunctional ethylenically unsaturated prepolymers which are known per se, can be initiated by means of free radicals and contain, for example, from 0.01 to 1.0 mol of polymerizable double bonds per 100 g of prepolymer, and have an average molecular weight of, for example, at least 400, in particular from 500 to 10,000. Depending on the intended application, however, prepolymers having higher molecular weights may also be suitable.

For example, polyesters containing polymerizable C—C double bonds and having a maximum acid number of 10, polyethers containing polymerizable C—C double bonds, hydroxyl-containing products of the reaction of a polyepoxide containing at least two epoxide groups per molecule with at least one α,β-ethylenically unsaturated carboxylic acid, polyurethane (meth)acrylates and α,β-ethylenically unsaturated acrylic copolymers containing acrylic radicals, as described in EP-A-12 339, are used. Mixtures of these prepolymers may also be used. Also suitable are the polymerizable prepolymers described in EP-A-33 896, which are thioether adducts of polymerizable prepolymers having an average molecular weight of at least 600, a carboxyl group content of from 0.2 to 15% and a content of from 0.01 to 0.8 mol of polymerizable C—C double bonds per 100 g of prepolymer. Other suitable aqueous dispersions based on specific alkyl (meth)acrylate polymers are described in EP-A-41 125, and suitable water-dispersible, radiation-curable prepolymers made from urethane acrylates are disclosed in DE-A-2 936 039.

These radiation-curable, aqueous prepolymer dispersions may contain, as further additives, dispersion assistants, emulsifiers, antioxidants, light stabilizers, dyes, pigments, fillers, for example talc, gypsum, silica, rutile, carbon black, zinc oxide and iron oxides, reaction accelerators, levelling agents, lubricants, wetting agents, thickeners, matting agents, antifoams and other assistants which are conventional in surface-coating technology. Suitable dispersion assistants are water-soluble, high molecular weight organic compounds containing polar groups, for example polyvinyl alcohols, polyvinylpyrrolidone and cellulose ethers. Emulsifiers which can be used are nonionic emulsifiers and possibly also ionic emulsifiers.

The photopolymerizable compositions contain the photoinitiator (b) judiciously in a quantity of from 0.05 to 15% by weight, preferably from 0.1 to 5% by weight, based on the composition.

In certain cases it may be of advantage, in addition to the molecular complex photoinitiator compound of the invention, to use other known photoinitiators, for example benzophenone, benzophenone derivatives, acetophenone, acetophenone derivatives, for example α-hydroxycycloalkyl phenyl ketone, dialkoxyacetophenone, α-hydroxy- or α-aminoacetophenone, 4-aroyl-1,3-dioxolane, benzoin alkyl ethers and benzil ketals, mono-acylphosphine oxides, bisacylphosphine oxides, ferrocenes or titanocenes.

When the molecular complex photoinitiators according to the invention are employed in hybrid systems, cationic photoinitiators such as benzoyl peroxide, aromatic sulfonium, phosphonium or iodonium salts or cyclopentadienylareneiron(II) complex salts are used in addition to the free-radical curing agents according to the invention.

The photopolymerizable compositions can be used for various purposes, for example as printing inks, as varnishes or clearcoats, as white paints, for example for wood or metal, as coating compositions, inter alia, for paper, wood, metal or plastic, as daylight-curable coatings for buildings and roadmarking, for photographic reproduction processes, for holographic recording materials, for image recording processes or for the production of printing plates which can be developed using organic solvents or aqueous-alkaline media, for the production of masks for screen printing, as dental filling materials, as adhesives, as pressure-sensitive adhesives, as laminating resins, as etch resists or permanent resists and as solder masks for electronic circuits, for the production of three-dimensional articles by bulk curing (UV curing in transparent moulds) or by the stereolithography process, as described, for example, in U.S. Pat. No. 4,575, 330, for the preparation of composite materials (for example styrenic polyesters, which may contain glass fibres and other assistants) and other thick-layer compositions, for the coating or encapsulation of electronic components or as coatings for optical fibres.

The molecular complex compounds according to the invention may also be used as initiators for emulsion polymerizations, as initiators of a polymerization for the fixing of ordered states of liquid-crystalline mono- and oligomers, and as initiators for the fixing of dyes to organic materials.

In surface coatings, mixtures of a prepolymer with polyunsaturated monomers are often used which also contain a monounsaturated monomer. The prepolymer here is primarily responsible for the properties of the coating film, and variation thereof allows the person skilled in the art to influence the properties of the cured film. The polyunsaturated monomer functions as a crosslinking agent which renders the coating film insoluble. The monounsaturated monomer functions as a reactive diluent by means of which the viscosity is reduced without the need to use a solvent.

Unsaturated polyester resins are mostly used in two-component systems in conjunction with a monounsaturated monomer, preferably styrene. For photoresists, specific one-component systems are frequently employed, for example polymaleimides, polychalcones or polyimides, as described in DE-A 2 308 830.

The molecular complex compounds according to the invention can additionally be used as free-radical photoinitiators or photoinitiating systems for radiation-curable powder coatings. The powder coatings can be based on solid resins and on monomers containing reactive double bonds, for example maleates, vinyl ethers, acrylates, acrylamides and mixtures thereof. A free-radically UV-curable powder coating can be formulated by mixing unsaturated polyester resins with solid acrylamides (e.g. methyl methacrylamidoglycolate) and with a free-radical photoinitiator according to the invention, as described, for example, in the paper "Radiation Curing of Powder Coating", Conference Proceedings, Radtech Europe 1993 by M. Wittig and Th. Gohmann. Similarly, free-radically UV-curable powder coatings can be formulated by mixing unsaturated polyester resins with solid acrylates, methacrylates or vinyl ethers and with a photoinitiator according to the invention. The powder coatings may also comprise binders as described, for example, in DE-A-42 28 514 and EP-A-636 669. The UV-curable powder coatings may also comprise white or coloured pigments. Thus, for example, preferably rutile titanium dioxide can be employed in concentrations of up to 50% by weight in order to give a cured powder coating having good covering power. The process normally comprises electrostatic or tribostatic spraying of the powder onto the substrate, for example metal or wood, melting of the powder by heating and, after a smooth film has been formed, radiation-curing of the coating using ultraviolet and/or visible light, for example with medium-pressure mercury lamps, metal halide lamps or xenon lamps. A particular advantage of the radiation-curable powder coatings over their heat-curable counterparts is that the flow time after the melting of the powder particles can be selectively extended in order to ensure the formation of a smooth, high-gloss coating. In contrast to heat-curable systems, radiation-curable powder coatings can be formulated without the unwanted effect of a reduction in their lifetime, so that they melt at relatively low temperatures. For this reason, they are also suitable as coatings for heat-sensitive substrates such as wood or plastics. In addition to the molecular complex photoinitiators according to the invention, the powder coating formulations may also include UV absorbers. Appropriate examples have been listed above under sections 1.–8.

The photocurable compositions according to the invention are suitable, for example, as coating substances for substrates of all kinds, for example wood, textiles, paper, ceramic, glass, plastics such as polyesters, polyethylene terephthalate, polyolefins or cellulose acetate, tate, especially in the form of films, and also metals such as Al, Cu, Ni, Fe, Zn, Mg or Co and GaAs, Si or $SiO_2$, on which it is desired to apply a protective coating or, by imagewise exposure, an image.

The substrates can be coated by applying a liquid composition, a solution or suspension to the substrate. The choice of the solvent and the concentration depend predominantly on the type of composition and the coating process. The solvent should be inert: in other words it should not undergo any chemical reaction with the components and should be capable of being removed again after the coating operation, in the drying process. Examples of suitable solvents are ketones, ethers and esters, such as methyl ethyl ketone, isobutyl methyl ketone, cyclopentanone, cyclohexanone, N-methylpyrrolidone, dioxane, tetrahydrofuran, 2-methoxyethanol, 2-ethoxyethanol, 1-methoxy-2-propanol, 1,2-dimethoxyethane, ethyl acetate, n-butyl acetate and ethyl 3-ethoxypropionate. Using known coating processes, the solution is applied evenly to a substrate, for example by spin coating, dip coating, knife coating, curtain coating, brushing, spraying—especially electrostatic spraying—and reverse roll coating. It is also possible to apply the photosensitive layer to a temporary, flexible support and then to coat the final substrate, for example a copper-laminated circuit board, by means of layer transfer via lamination.

The quantity applied (layer thickness) and the nature of the substrate (layer support) are functions of the desired application. The range of coat thicknesses generally comprises values from about 0.1 µm to more than 10 µm.

The radiation-sensitive compositions according to the invention find application as negative resists which have a very high photosensitivity and can be developed in an aqueous-alkaline medium without swelling. They are suitable as photoresists for electronics (galvano-resists, etch resists and solder resists), the production of printing plates such as offset printing plates or screen printing forms, and can be used for chemical milling or as microresists in the production of integrated circuits. There is a correspondingly wide range of variation in the possible layer supports and the processing conditions for the coated substrates. Examples of the layer supports for photographic information recording are films made of polyester, cellulose acetate or plastic-coated paper; for offset printing plates, specially treated aluminium; for the production of printed circuits, copper-faced laminates, and for the production of integrated circuits, silicon wafers. The layer thicknesses for photographic materials and offset printing plates are generally from about 0.5 µm to 10 µm, while for printed circuits they are from 0.4 µm to about 2 µm.

Following the coating of the substrates, the solvent is generally removed by drying to leave a layer of the photoresist on the substrate.

The term "imagewise exposure" relates both to exposure through a photomask containing a predetermined pattern, for example a slide, exposure by a laser beam which is moved under control from a computer, for example, over the surface of the coated substrate, thereby generating an image, and to irradiation with computer-controlled electron beams.

Following the imagewise exposure of the material and prior to developing, it may be advantageous to carry out a brief thermal treatment, in which only the exposed parts are thermally cured. The temperatures employed are generally 50–150° C. and preferably 80–130° C.; the duration of the thermal treatment is generally between 0.25 and 10 minutes.

The photocurable composition can also be used in a process for the production of printing plates or photoresists as described, for example, in DE-A-40 13 358. In this process the composition is exposed before, simultaneously with or after the imagewise irradiation, exposure being carried out for a short period with visible light having a wavelength of at least 400 nm without a mask.

Following exposure and the optional thermal treatment, the unexposed areas of the photo-resist are removed using a developer in a manner known per se.

As already mentioned, the compositions according to the invention can be developed by aqueous-alkaline media. Suitable aqueous-alkaline developer solutions are, in particular, aqueous solutions of tetraalkylammonium hydroxides or of alkali metal silicates, phosphates, hydroxides and carbonates. Relatively small quantities of wetting agents and/or organic solvents may also be added, if desired, to these solutions. Examples of typical organic solvents which may be added in small quantities to the developing liquids are cyclohexanone, 2-ethoxyethanol, toluene, acetone and mixtures of such solvents.

Photocuring is of considerable importance for printing inks, since the drying time of the binder is a crucial factor for the production rate of graphic products and should be in the order of fractions of seconds. UV-curable inks are important, in particular, for screen printing.

As already mentioned, the mixtures according to the invention are also highly suitable for the production of printing plates, where, for example, mixtures of soluble, linear polyamides or styrene/butadiene or styrene/isoprene rubber, polyacrylates or polymethyl methacrylates containing carboxyl groups, polyvinyl alcohols or urethane acrylates are used with photopolymerizable monomers, for example acrylamides, methacrylamides, acrylates or methacrylates, and a photoinitiator. Films and plates made from these systems (wet or dry) are exposed through the negative (or positive) of the print original, and the uncured parts are subsequently washed out using a suitable solvent.

A further area of application for photocuring is in the coating of metals, for example in the coating of metal sheets and tubes, cans or bottle caps, and the photocuring of plastic coatings, for example PVC-based wall or floor coverings.

Examples of the photocuring of paper coatings are the colourless coating of labels, record sleeves or book covers.

The use of the compounds according to the invention for curing shaped articles made from composite compositions is likewise of interest. The composite composition is made up of a self-supporting matrix material, for example a glass-fibre fabric, or else, for example, plant fibres [cf. K.-P. Mieck and T. Reussmann in Kunststoffe 85 (1995), 366–370], which is impregnated with the photocuring formulation. Shaped articles which are produced from composite compositions, using the compounds according to the invention, are of high mechanical stability and resistance. The compounds according to the invention can also be used as photocuring agents in moulding, impregnating and coating compositions, as are described, for example, in EP-A-7086. Examples of such compositions are fine coating resins on which stringent requirements are placed with respect to their curing activity and resistance to yellowing, or fibre-reinforced mouldings such as planar or longitudinally or transversely corrugated light diffusing panels. Processes for the production of such mouldings, for example hand lay-up, spray lay-up, centrifugal or filament winding processes, are described by, for example, P. H. Selden in "Glasfaserverstärkte Kunststoffe" [Glass fibre-reinforced plastics], page 610, Springer Verlag Berlin-Heidelberg-New York 1967. Examples of articles which can be produced by this process are boats, chipboard or plywood panels coated on both sides with glass fibre-reinforced plastic, pipes, containers and the like. Other examples of moulding, impregnating and coating compositions are UP resin fine coatings for mouldings containing glass fibres (GRP), e.g. corrugated sheets and paper laminates. Paper laminates may also be based on urea or melamine resins. The fine coating is produced on a support (for example a sheet) prior to the production of the laminate. The photocurable compositions according to the invention can also be used for casting resins or for encapsulating articles such as electronic components and the like. Curing employs medium-pressure mercury lamps as are conventional in UV curing. However, less intense lamps are also of particular interest, for example those of the type TL 40W/03 or TL40W/05. The intensity of these lamps corresponds approximately to that of sunlight. It is also possible to employ direct sunlight for curing. A further advantage is that the composite composition can be removed in a part-cured, plastic state from the light source and can be shaped. Complete curing is carried out subsequently.

Also important is the use of photocurable compositions for imaging processes and for the optical production of information carriers. In these applications, the coat (wet or dry) applied to the support is irradiated—as already described above—with UV or visible light through a photomask and the unexposed areas of the coat are removed by treatment with a solvent (=developer). The photocurable layer can also be applied by electrodeposition to metal. The exposed areas are crosslinked/polymeric and thus insoluble and remain on the support. If appropriate coloration is carried out, visible images are formed. If the support is a metallized layer, then the metal can be removed from the unexposed areas by etching after exposure and development or can be increased in thickness by electroplating. In this way, printing electronic circuits and photoresists can be produced.

The photosensitivity of the compositions according to the invention generally ranges from the UV region (about 200 nm) up to about 600 nm. Suitable radiation comprises, for example, sunlight or light from artificial sources. Therefore, a large number of very different types of light source can be used. Both point sources and flat radiators (lamp carpets) are appropriate. Examples are carbon arc lamps, xenon arc lamps, medium-pressure, high-pressure and low-pressure mercury lamps, doped with metal halides if desired (metal halogen lamps), microwave-stimulated metal vapour lamps, excimer lamps, superactinic fluorescent tubes, fluorescent lamps, incandescent argon lamps, electronic flashlights, photographic flood lamps, electron beams and X-rays. The distance between the lamp and the substrate according to the invention which is to be coated can vary depending on the application and on the type and/or power of the lamp, for example between 2 cm and 150 cm. Also suitable, for example, are lasers in the visible range.

The invention therefore also provides a method for the photopolymerization of compounds having ethylenically unsaturated double bonds, which comprises irradiating a composition according to the invention as described above, with light in the range from 200 to 600 nm.

The invention also provides for the use of the above-described composition for the production of surface coating materials, printing inks, printing plates, dental compositions and resist materials and as image recording material, especially for holographic recordings.

The invention likewise provides a coated substrate which is coated on at least one surface with a composition as described above, and to a process for the photographic production of relief images, in which a coated substrate is subjected to imagewise exposure and then the unexposed portions are removed with a solvent. This exposure can take place either through a mask or by means of a laser beam without a mask.

The molecular complex compounds according to the invention can easily be incorporated into the formulations that are to be cured.

The molecular complex compounds according to the invention in general contain fewer impurities than the individual components, since in the course of the preparation the impurities remain in solution. These photoinitiators are therefore also suitable for very sensitive applications.

The molecular complex compounds according to the invention are of good stability on storage.

In preparing the molecular complex compounds it is also possible for mixtures to be formed between the molecular complex crystals according to the invention and one of the components used for their preparation, for example a mixture of molecular complex crystals consistings of compounds of the formula I and II and crystals of the compounds of the formula I.

These mixtures can also be employed as photoinitiators.

The examples which follow illustrate the invention in more detail. As in the remainder of the description and in the claims, parts or percentages are by weight unless stated otherwise.

EXAMPLE 1

Molecular Complex of bis(2,6-dimethoxybenzoyl)-2,4,4-trimethylpentyl-phosphine Oxide and α-hydroxycyclohexyl Phenyl Ketone To prepare seed crystals, bis(2,6-dimethoxybenzoyl)-2,4,4-trimethylpentylphosphine oxide and α-hydroxycyclohexyl phenyl ketone in a molar ratio of 1:1 are dissolved at 80° C. in a mixture of isooctane and ethyl acetate (weight ratio 2.3:1). Nucleation is initiated at 53–55° C. by rubbing on the glass wall using a glass rod until the crystallization process begins. The crystals obtained in this way are used as seed crystals in the first preparation of larger amounts of the molecular complex.

Preparation of larger amounts of the molecular complex crystals:

385 g of bis(2,6-dimethoxybenzoyl)-2,4,4-trimethylpentylphosphine oxide and 165 g of α-hydroxycyclohexyl phenyl ketone are dissolved in a mixture of 385 g of isooctane and 165 g of ethyl acetate at 80° C. The mixture is cooled to 53–55° C. The emulsion present is seeded at this temperature with the corresponding mixed-crystal modification, and crystallized. After filtration at 20° C., the product is washed with the solvent mixture and is dried at about 70° C. and 50 mbar, to give 530 g of dry crystalline product, i.e. 96% of theory. The melting point (determined by Differential Scanning Calorimetry) is 90° C. The phosphorus content is 4.47%. The content of bis(2,6-dimethoxybenzoyl)-2,4,4-trimethylpentylphosphine oxide is 71%, that of α-hydroxycyclohexyl phenyl ketone 29%. These values are determined by High Pressure Liquid Chromatography (HPLC).

X-ray structural analysis (measured on a yellow platelet-shaped crystal using a four-circle diffractometer Philips PW1100, MoKα$_1$ radiation (λ=0.70926 Å), calculated by direct methods using the program system SHELX86 (Sheldrick, Göttingen), indicates a monoclinic crystal system having the space group P2$_1$/c (International Tables for X-ray Crystallography, 1974, Vol. IV).

Formula $C_{26}H_{35}O_7P.C_{13}H_{16}O_2$; molecular weight 694.80

The unit cell contains 4 molecules and its dimensions are as follows:

a (Å) 17.514(2); b (Å) 10.518(1); c (Å) 20.912(2);

β (°) 97.92(1); V (Å$^3$) 3815.5(8).

The refinement calculation gives an R value of 0.047.

EXAMPLE 2

Molecular Complex of bis(2,6-dimethoxybenzoyl)-2,4,4-trimethylpentyl-phosphine Oxide and α-hydroxycyclohexyl Phenyl Ketone The seed crystals are prepared as described in Example 1. 140 g of bis(2,6-dimethoxybenzoyl)-2,4,4- trimethylpentylphosphine oxide and 60 g of α-hydroxycyclohexyl phenyl ketone are dissolved at 30–35° C. in a mixture of 92 g of methyl ethyl ketone (MEK) and 11 g of water. (The presence of water here is not mandatory; the complex is also obtained if pure MEK is used). The solution is cooled to 20–23° C. and seeded with the appropriate mixed-crystal modification. As soon as a distinct crystal suspension has formed, it is slowly diluted with 500 ml of water. Filtration at 20° C. gives 220 g of a moist product which is washed with water and dried at about 70° C. and 50 mbar, to give 200 g, i.e. >99% of theory, of dry crystalline product having a melting point of 91° C. (DSC). The content of bis(2,6-dimethoxybenzoyl)-2,4,4-trimethylpentylphosphine oxide is 71%, that of α-hydroxycyclohexyl phenyl ketone 29% (HPLC).

EXAMPLE 3

Molecular Complex of bis(2,6-dimethoxybenzoyl)-2,4,4-trimethylpentyl-phosphine Oxide and 2-hydroxy-2-methyl-1-phenylpropan-1-one Seed crystals are prepared by dissolving the components in a molar ratio of 1:1 in ethyl acetate at room temperature. Crystallization is brought about by adding hexane. A mixture is formed of molecular complex crystals consisting of bis(2,6-dimethoxybenzoyl)-2,4,4-trimethylpentylphosphine oxide and 2-hydroxy-2-methyl-1-phenylpropan-1-one and crystals consisting of bis(2,6-dimethoxybenzoyl)-2,4,4-trimethylpentylphosphine oxide. This crystal mixture is suitable as a seed crystal in the preparation of larger amounts of crystals of the molecular complex.

Preparation of larger amounts of the molecular complex crystals:

150 g of bis(2,6-dimethoxybenzoyl)-2,4,4-trimethylpentylphosphine oxide and 50 g of 2-hydroxy-2-methyl-1-phenylpropan-1-one are dissolved at 30–35° C. in a mixture of 92 g of methyl ethyl ketone and 11 g of water. (The presence of water is not mandatory here: the complex is also obtained if pure MEK is used). The solution is cooled to 5° C. and is seeded with the corresponding mixed-crystal modification. As soon as a distinct crystal suspension has formed, at 5° C., it is diluted slowly with 1000 ml of water. Filtration at 20° C. and drying at about 60° C. and 50 mbar give 194 g of dry crystalline product, i.e. 97% of theory, having a melting point of 73° C. (DSC) and a phosphorus contents of 4.7%.

X-ray structural analysis (measured on a platelet-shaped colourless crystal using a four-circle diffractometer Philips PW1100, MoKα$_1$ radiation (λ=0.70926 Å), calculated using direct methods with the program system SHELX86 (Sheldrick, Göttingen), indicates a monoclinic crystal system having the space group P2$_1$/n (International Tables for X-ray Crystallography, 1974, Vol. IV).

Formula $C_{26}H_{35}O_7P.C_{10}H_{12}O_2$; molecular weight 654.73.

The unit cell contains 4 molecules, and its dimensions are as follows:

a (Å) 17.828(2); b (Å) 10.365(1); c (Å) 19.592(2);
β (°) 95.46(1); V (Å$^3$) 3603.9(8).

The refinement calculation gives an R value of 0.042.

EXAMPLE 4

Molecular Complex of bis(phenyl)-2,4,6-trimethylbenzoylphosphine Oxide and α-hydroxycyclohexyl Phenyl Ketone Seed crystals are prepared by very slowly cooling a solution of bis(phenyl)-2,4,6-trimethyl-benzoylphosphine oxide and α-hydroxycyclohexyl phenyl ketone in a molar ratio of 1:1 in ®Isopar E (mixture of branched and unbranched paraffinic hydrocarbons; ESSO).

Preparation of larger amounts of the molecular complex crystals 100 g of bis(phenyl)-2,4,6-trimethylbenzoylphosphine oxide and 59 g of α-hydroxycyclohexylphenyl ketone are dissolved at 80° C. in 200 ml of ®Isopar E. The resulting solution is cooled to 55° C., during which a cloudy emulsion is formed. This emulsion is seeded at 53–55° C. with the corresponding mixed-crystal modification. The product crystallizes out in the form of hard, pale yellow crystals. The resulting suspension is cooled to room temperature at a uniform rate over the course of from 2 to 3 hours and then is filtered. The filter cake is washed first with ®Isopar E and then with hexane. Drying at 50° C. and 50 mbar gives 150 g of the product, corresponding to 94.3% of theory. The melting point is 69.4° C. (DSC), the phosphorus content 5.5%.

X-ray structural analysis (measured using a four-circle diffractometer Philips PW1100, MoKα$_1$ radiation (λ=0.70926 Å), calculated by direct methods using the program system SHELX86 (Sheldrick, Göttingen), indicates a triclinic crystal system having the space group Pl, centrosymmetric (No.2 in International Tables for X-ray Crystallography, 1974, Vol. IV).

Formula: $C_{22}H_{21}O_2P.C_{13}H_{16}O_2$; molecular weight 552.65.

The unit cell contains 2 molecules and its dimensions are as follows:

a (Å) 9.081; b (Å) 11.436; c (Å) 16.092;
α (°) 91.98; β (°) 101.05; γ (°) 109.50; V (Å$^3$) 1537.3.

The refinement calculation gives an R value of 0.051.

The distance between the two O atoms associated via a hydrogen bond (OH group of the hydroxy ketone with the O atom on the phosphorus of the phosphine oxide) is 2.715 Å. The bond angle O—H..O is measured as 169°.

EXAMPLE 5

Molecular Complex of bis(phenyl)-2,4,6-trimethylbenzoylphosphine Oxide and α-hydroxycyclohexyl Phenyl Ketone (Melt Method)

10 g of bis(phenyl)-2,4,6-trimethylbenzoylphosphine oxide and 5.9 g of α-hydroxycyclohexyl phenyl ketone are melted at 100° C., homogenized and allowed to cool slowly to room temperature. Seeding with the corresponding molecular complex compound brings about spontaneous crystallization.

EXAMPLE 6

Molecular Complex of bis(2,4,6-trimethylbenzoyl)-2,4-dihexoxyphenylphosphine Oxide and α-hydroxycyclohexyl Phenyl Ketone (Melt Method)

Seed crystals are obtained by very slowly cooling a 1:1 molar melt of bis(2,4,6-trimethylbenzoyl)-2,4-dihexoxyphenylphosphine oxide and α-hydroxycyclohexyl phenyl ketone and intensively scratching on the wall of the flask after the melt has cooled.

Preparation by crystallization 1.5 g of bis(2,4,6-trimethylbenzoyl)-2,4-dihexoxyphenylphosphine oxide and 0.5 g of α-hydroxycyclohexyl phenyl ketone are dissolved at 50–60° C. in 10 ml of ®Isopar E/ethyl ester (3:1). The resulting solution is cooled to 20–25° C. and is seeded with seed crystals as described above. The solution is then stored overnight in a refrigerator. During this time, the product crystallizes out in the form of pale yellow crystals. The resulting suspension is filtered and the filter cake is washed first with cold Isopar® E and then with cold hexane.

Drying at 40–50° C. and 50 mbar gives 1 g of the product (about 50% of theory). The melting point is determined by the DSC method is 67.3° C.

X-ray structural analysis (measured on a cubic crystal using a four-circle diffractometer Nonius CAD4 (Enraf Nonius), CuK$\alpha_1$ radiation ($\lambda$=1.54178 Å), calculated by direct methods using the program system SHELX86 (Sheldrick, Göttingen), indicates a triclinic crystal system having the space group P-1 (International Tables for X-ray Crystallography, 1974, Vol. IV).

Formula: $C_{38}H_{51}O_5P \cdot C_{13}H_{16}O_2$; molecular weight 823.02.

The unit cell contains 2 molecules and its dimensions are as follows:

a (Å) 11.721 (1); b (Å) 12.327(1); c (Å) 17.493(1);

$\alpha$ (°) 105.73(1); $\beta$ (°) 99.32(1); $\gamma$ (°) 92.71(1); V (Å$^3$) 2389.6(3).

The refinement calculation gives an R value of 0.079.

The distance between the two O atoms associated via a hydrogen bond (OH group of the hydroxy ketone with O atom on the phosphorus of the phosphine oxide) is 2.747 Å. The bond angle O—H..O is measured as 169°.

EXAMPLE 7

Curing of a White Paint

A photocurable white paint is prepared by mixing the following components:

| | |
|---|---|
| 67.5% | Ebecryl ® 830 |
| 5.0% | hexanediol diacylate |
| 2.5% | trimethylolpropane triacrylate |
| 25.0% | RTC-2 ® Titanium dioxide and |
| 3.0% | molecular complex compound from Example 3. |

The formulation is applied to chipboard panels using a 100 μm slotted doctor knife. Exposure is then carried out with an 80 W/cm medium-pressure mercury lamp of the Canrad-Hanovia type (USA), the sample being passed under the lamp by belt at a speed of 5 m/min. The resulting paint film is fully through cured and resistant to smearing, and its pendulum hardness (in accordance with König, DIN 53157) is 146 seconds.

What is claimed is:

1. A molecular complex compound comprising a mono-, bis- or trisacylphosphine oxide compound with an α-hydroxy ketone compound in crystalline form associated by way of hydrogen bonds between the hydrogen atoms of the hydroxyl groups in said hydroxy-ketone compound and oxygen atoms attached to phosphorous in said phosphine oxide compound.

2. A molecular complex compound according to claim 1, wherein the mono-, bis- or trisacylphosphine oxide compound is a compound of the formula I

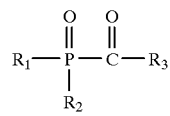

in which $R_1$ and $R_2$ independently of one another are $C_1$–$C_{12}$alkyl, benzyl, phenyl which is unsubstituted or substituted from one to four times by halogen, $C_1$–$C_8$alkyl and/or $C_1$–$C_8$alkoxy, or are cyclohexyl or a group $COR_3$; or $R_1$ is —$OR_4$, or a group

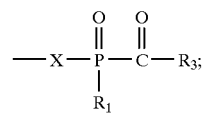

$R_3$ is phenyl which is unsubstituted or substituted from one to four times by $C_1$–$C_8$alkyl, $C_1$–$C_8$alkoxy, $C_1$–$C_8$alkylthio and/or halogen, or is a group

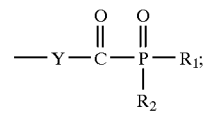

$R_4$ is $C_1$–$C_8$alkyl, phenyl or benzyl;

Y is phenylene, $C_1$–$C_{12}$alkylene or cyclohexylene; and

X is $C_1$–$C_{18}$alkylene or a group

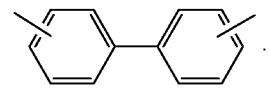

3. A molecular complex compound according to claim 1, wherein the α-hydroxy ketone compound is a compound of the formula II

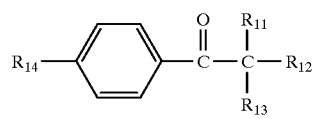

in which $R_{11}$ and $R_{12}$ independently of one another are hydrogen, $C_1$–$C_6$alkyl or phenyl, or $R_{11}$ and $R_{12}$, together with the carbon atom to which they are attached, form a cyclohexyl ring;

$R_{13}$ is OH;

$R_{14}$ is hydrogen, $C_1$–$C_{12}$alkyl, $C_1$–$C_{12}$alkoxy, —OCH$_2$CH$_2$—OR$_{15}$, a group CH$_2$=C(CH$_3$)— or

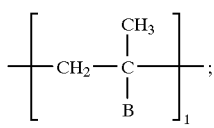

I is a number from 2 to 10;
B is the radical

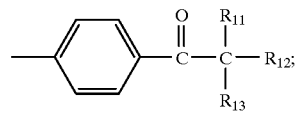

and
$R_{15}$ is hydrogen,

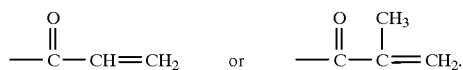

4. A molecular complex compound according to claim 1, comprising a mono- or bisacylphosphine oxide compound of the formula I

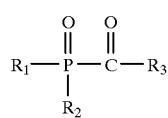

(I)

in which
$R_1$ and $R_2$ independently of one another are $C_1$–$C_{12}$alkyl, phenyl which is unsubstituted or substituted once or twice by $C_1$–$C_8$alkyl and/or $C_1$–$C_8$alkoxy, or are $COR_3$;
$R_3$ is a radical

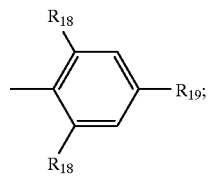

$R_{18}$ is $C_1$–$C_4$alkyl or $C_1$–$C_4$alkoxy; and
$R_{19}$ is hydrogen or $C_1$–$C_4$alkyl;
and an α-hydroxy ketone compound of the formula II

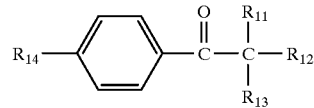

(II)

in which
$R_{11}$ and $R_{12}$ independently of one another are $C_1$–$C_4$alkyl or $R_1$ and $R_2$, together with the carbon atom to which they are attached, form a cyclohexyl ring; and $R_{14}$ is hydrogen.

5. A molecular complex compound according to claim 1, wherein the acylphosphine oxide compound is bis(2,6-dimethoxybenzoyl)(2,4,4-trimethylpentyl)phosphine oxide or 2,4,6-trimethylbenzoyldiphenylphosphine oxide and the α-hydroxy ketone compound is a compound of the formula II in which $R_{11}$ and $R_{12}$ are $C_1$–$C_4$alkyl or $R_{11}$ and $R_{12}$, together with the C atom to which they are attached, form a cyclohexyl ring, $R_{13}$ is OH and $R_{14}$ is hydrogen.

6. A molecular complex compound according to claim 1, wherein the acylphosphine oxide compound is bis(2,6-dimethoxybenzoyl)(2,4,4-trimethylpentyl)phosphine oxide, bis(2,4,6-trimethylbenzoyl)(2,4-dihexyloxyphenyl) phosphine oxide, bis(2,4,6-trimethyl-benzoyl)(4-ethoxyphenyl)phosphine oxide or 2,4,6-trimethylbenzoyldiphenylphosphine oxide and the α-hydroxy ketone compound is α-hydroxycyclohexyl phenyl ketone or 2-hydroxy-2-methyl-1-phenylpropan-1-one.

7. A molecular complex compound according to claim 1, comprising the mono-, bis- or trisacylphosphine oxide compound and the α-hydroxy ketone compound in a molar ratio of 1:1.

8. A photopolymerizable composition comprising
(a) at least one ethylenically unsaturated photopolymerizable compound, and
(b) as photoinitiator, at least one molecular complex compound according to claim 1.

9. A photopolymerizable composition according to claim 8, which comprises other additives in addition to component (b).

10. A photopolymerizable composition according to claim 8, containing 0.015–15 in particular 0.2–5% by weight of component (b) as photoinitiator.

11. A photopolymerizable composition according to claim 8 containing 0.2–5% by weight of component (b) as photoinitiator.

12. A photopolymerizable composition according to claim 8, comprising as photoinitiator at least one molecular complex compound according to claim 1 and also a UV absorber selected from the group consisting of the hydroxyphenyl-s-triazines and/or hydroxyphenylbenzotriazoles and/or sterically hindered amines based on 2,2,6,6-tetramethylpiperidines.

13. A method of photopolymerizing compounds having ethylenically unsaturated double bonds, which comprises irradiating a composition according to claim 8 with light in the range from 200 to 600 nm.

14. A method according to claim 13 for producing paints, printing inks, printing plates, dental compositions, resist materials and image recording materials, which comprises incorporating into or applying to said materials a composition according to claim 8 and irradiating the resulting formulation with light in the range from 200 to 600 nm.

15. A method according to claim 13 for producing holographic recordings which comprises incorporating into or applying to said holographic recordings a composition according to claim 8 and irradiating the resulting formulation with light in the range from 200 to 600 nm.

16. A coated substrate which is coated on at least one surface with a composition according to claim 8.

17. A process for the photographic production of relief images, in which a coated substrate according to claim 16 is subjected to imagewise exposure and then the unexposed portions are removed with a solvent.

* * * * *